United States Patent
Schulte et al.

(10) Patent No.: US 11,971,911 B2
(45) Date of Patent: *Apr. 30, 2024

(54) SYSTEMS AND METHODS FOR CUSTOMIZED ANNOTATION OF MEDICAL INFORMATION

(71) Applicant: Apixio, LLC, San Mateo, CA (US)

(72) Inventors: Darren Matthew Schulte, San Francisco, CA (US); John O. Schneider, Los Gatos, CA (US); Robert Derward Rogers, Oakland, CA (US); Vishnuvyas Sethumadhavan, Mountain View, CA (US)

(73) Assignee: Apixio, LLC, San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/879,637

(22) Filed: Aug. 2, 2022

(65) Prior Publication Data

US 2022/0398270 A1    Dec. 15, 2022

Related U.S. Application Data

(63) Continuation of application No. 16/784,099, filed on Feb. 6, 2020, now Pat. No. 11,403,330, which is a
(Continued)

(51) Int. Cl.
*G06F 16/31* (2019.01)
*G16H 10/60* (2018.01)
*G16H 15/00* (2018.01)

(52) U.S. Cl.
CPC .......... *G06F 16/313* (2019.01); *G16H 10/60* (2018.01); *G16H 15/00* (2018.01)

(58) Field of Classification Search
CPC ...... G06F 16/313; G06F 16/35; G06F 16/383; G16H 10/60; G16H 15/00; G16H 20/30; G16H 50/20; G16H 50/30; G06Q 10/10
See application file for complete search history.

(56) References Cited

U.S. PATENT DOCUMENTS 5,307,262 A    4/1994   Ertel
7,321,861 B1    1/2008   Oon
(Continued)

FOREIGN PATENT DOCUMENTS

JP    H1145304 A    2/1999
JP    2001290890 A    10/2001
(Continued)

OTHER PUBLICATIONS

Hayeems, Robin Zoe. Informed consent and genetic databases: An exploration of the authorization model ProQuest Dissertations and Theses. ProQuest Dissertations Publishing. (2007)) (Year: 2007).*
(Continued)

*Primary Examiner* — Linh Giang Le
(74) *Attorney, Agent, or Firm* — Armstrong Teasdale LLP

(57) ABSTRACT

Systems and methods for generating customized annotations of a medical record are provided. The system receives a medical record and processes it using a predictive model to identify evidence of a finding. The system then determines whether to have a recall enhancement or validation of a specific finding. Recall enhancement is used to tune or develop the predictive model, while validation is used to rapidly validate the evidence. The source document is provided to the user and feedback is requested. When asking for validation, the system also highlights the evidence already identified and requests the user to indicate if the evidence is valid for a particular finding. If recall enhancement is utilized, the source document is provided and the user is asked to find evidence in the document for a particular finding. The user may then highlight the evidence that supports the finding. The user may also annotate the evidence using free form text.

20 Claims, 19 Drawing Sheets

Related U.S. Application Data continuation of application No. 14/538,798, filed on Nov. 11, 2014, now Pat. No. 10,580,520, which is a continuation-in-part of application No. 13/656,652, filed on Oct. 19, 2012, now Pat. No. 8,898,798, which is a continuation-in-part of application No. 13/223,228, filed on Aug. 31, 2011, now Pat. No. 10,176,541, said application No. 14/538,798 is a continuation-in-part of application No. 14/498,594, filed on Sep. 26, 2014, now Pat. No. 10,600,504.

(60) Provisional application No. 62/059,139, filed on Oct. 2, 2014, provisional application No. 61/379,228, filed on Sep. 1, 2010, provisional application No. 61/682,217, filed on Aug. 11, 2012, provisional application No. 61/883,967, filed on Sep. 27, 2013.

(56) References Cited

U.S. PATENT DOCUMENTS

| | | |
| --- | --- | --- |
| 8,898,798 B2 | 11/2014 | Rogers et al. |
| 10,580,520 B2 | 3/2020 | Schulte et al. |
| 10,629,303 B2 | 4/2020 | Schulte et al. |
| 2001/0042080 A1 | 11/2001 | Ross |
| 2002/0010679 A1 | 1/2002 | Felsher |
| 2002/0188182 A1 | 12/2002 | Haines et al. |
| 2003/0046280 A1 | 3/2003 | Rotter et al. |
| 2003/0229510 A1 | 12/2003 | Kerr |
| 2004/0073458 A1 | 4/2004 | Jensen |
| 2004/0076264 A1 | 4/2004 | Sorenson |
| 2004/0109028 A1 | 6/2004 | Stern et al. |
| 2004/0249667 A1 | 12/2004 | Oon |
| 2005/0043986 A1 | 2/2005 | McConnell et al. |
| 2005/0138017 A1 | 6/2005 | Keen et al. |
| 2005/0228593 A1 | 10/2005 | Jones |
| 2005/0251422 A1 | 11/2005 | Wolfman et al. |
| 2006/0036619 A1 | 2/2006 | Fuerst |
| 2006/0047669 A1 | 3/2006 | Durrence |
| 2006/0112050 A1 | 5/2006 | Miikkulainen et al. |
| 2006/0129435 A1 | 6/2006 | Smitherman |
| 2007/0016450 A1 | 1/2007 | Bhora et al. |
| 2007/0055545 A1 | 3/2007 | Maughan et al. |
| 2007/0106754 A1 | 5/2007 | Moore |
| 2007/0192143 A1 | 8/2007 | Krishnan et al. |
| 2007/0192910 A1 | 8/2007 | Vu et al. |
| 2007/0219829 A1 | 9/2007 | Kay |
| 2007/0226211 A1 | 9/2007 | Heinze et al. |
| 2007/0299651 A1* | 12/2007 | Koll ............... G16H 10/60 704/235 |
| 2008/0077443 A1 | 3/2008 | Singer |
| 2008/0091633 A1 | 4/2008 | Rappaport |
| 2008/0103828 A1 | 5/2008 | Squilla et al. |
| 2008/0120296 A1 | 5/2008 | Kariathungal |
| 2008/0250025 A1 | 10/2008 | Abhyanker |
| 2008/0256181 A1* | 10/2008 | Morita ............ G16H 10/60 709/204 |
| 2008/0263048 A1 | 10/2008 | Wise |
| 2008/0270340 A1 | 10/2008 | Abrams |
| 2009/0024615 A1 | 1/2009 | Pedro |
| 2009/0070103 A1 | 3/2009 | Beggelman |
| 2009/0112882 A1 | 4/2009 | Maresh |
| 2009/0136102 A1 | 5/2009 | Kimpe |
| 2009/0138287 A1 | 5/2009 | Hermann, Jr. |
| 2009/0228303 A1 | 9/2009 | Faulkner et al. |
| 2009/0228909 A1 | 9/2009 | Huang |
| 2009/0259487 A1 | 10/2009 | Rao et al. |
| 2009/0271221 A1 | 10/2009 | Aridi |
| 2009/0287504 A1 | 11/2009 | Benjamin et al. |
| 2010/0036680 A1 | 2/2010 | Familant |
| 2010/0088107 A1 | 4/2010 | Ur et al. |
| 2010/0117799 A1 | 5/2010 | Dormer |
| 2010/0131299 A1 | 5/2010 | Hasan |
| 2010/0169123 A1 | 7/2010 | Maus |
| 2010/0179827 A1 | 7/2010 | McCallie, Jr. et al. |
| 2010/0185496 A1 | 7/2010 | Hahn |
| 2010/0235410 A1 | 9/2010 | Apacible et al. |
| 2010/0324936 A1 | 12/2010 | Vishnubhatla |
| 2011/0078145 A1 | 3/2011 | Chung et al. |
| 2011/0117799 A1 | 5/2011 | Harada et al. |
| 2011/0295616 A1 | 12/2011 | Vesto |
| 2012/0060216 A1 | 3/2012 | Chaudhri et al. |
| 2012/0066017 A1 | 3/2012 | Siegel |
| 2012/0166212 A1 | 6/2012 | Campbell |
| 2012/0215578 A1 | 8/2012 | Frank et al. |
| 2012/0284056 A1 | 11/2012 | Hofstetter |
| 2012/0303378 A1 | 11/2012 | Lieberman |
| 2013/0124523 A1 | 5/2013 | Rogers et al. |
| 2013/0159023 A1 | 6/2013 | Srinivas et al. |
| 2013/0238349 A1 | 9/2013 | Sethumadhavan et al. |
| 2013/0297536 A1 | 11/2013 | Almosni et al. |
| 2013/0332194 A1 | 12/2013 | DAuria et al. |
| 2013/0332199 A1 | 12/2013 | Freiwat et al. |
| 2013/0346356 A1 | 12/2013 | Welinder et al. |
| 2014/0012738 A1 | 1/2014 | Woo |
| 2014/0046697 A1 | 2/2014 | Rogers et al. |
| 2014/0136559 A1 | 5/2014 | Kottaram |
| 2014/0257842 A1 | 9/2014 | Heinze et al. |
| 2014/0278832 A1 | 9/2014 | Glavina et al. |
| 2015/0066537 A1 | 3/2015 | Sheffer et al. |
| 2015/0066539 A1 | 3/2015 | Sheffer et al. |
| 2015/0095065 A1 | 4/2015 | Schneider et al. |
| 2015/0142472 A1 | 5/2015 | Schulte et al. |
| 2015/0269337 A1 | 9/2015 | Schulte et al. |
| 2016/0048643 A1 | 2/2016 | Woods et al. |
| 2017/0132314 A1 | 5/2017 | Liu et al. |

FOREIGN PATENT DOCUMENTS

| | | | |
| --- | --- | --- | --- |
| JP | 2001325290 A | 11/2001 | |
| JP | 2002318820 A | 10/2002 | |
| JP | 2003263507 A | 9/2003 | |
| JP | 2004280807 A | 10/2004 | |
| JP | 2005309666 A | 11/2005 | |
| JP | 2006107299 A | 4/2006 | |
| JP | 2006164234 A | 6/2006 | |
| JP | 2007193399 A | 8/2007 | |
| JP | 2007323525 A | 12/2007 | |
| JP | 2008204378 A | 9/2008 | |
| JP | 2009193157 A | 8/2009 | |
| KR | 1020050015059 A | 2/2005 | |
| KR | 1020090050881 A | 5/2009 | |
| WO | 0154042 A1 | 7/2001 | |
| WO | 2007051245 A1 | 5/2007 | |
| WO | 2008039880 A2 | 4/2008 | |
| WO | 2010058398 A2 | 5/2010 | |
| WO | WO-2010058398 A2 * | 5/2010 | ........... A61B 1/0005 |

OTHER PUBLICATIONS

Hayeerns Robin Zoe. Informed consent and genetic databases: An exploration of the authorization model ProQuest Dissertations Publishing. (2007).

Lemeshow et al., Searching one or two databases was insufficient for meta-analysis of observational studies, 7 pages (Year: 2005).

Valkhoff, Vera E.; Coloma, Preciosa; Mosseveld, Mees; Kuipers, Ernst J.; Sturkenboom, Miriam C.; Trifiro, GianlucaValidation of the Diagnosis for Upper Gastrointestinal Bleeding in a Dutch Medical Record Database Gastroenterology 142.5, Suppl. 1: S507. May 2012 (Year: 2012).

Vazquez, Miguel 1 ; Krallinger, Martin 1 ; Leitner, Florian 1 ; Valencia, Alfonso. Text Mining for Drugs and Chemical Compounds: Methods, Tools and Applications. 1 1 Ctr Nacl Invest Oncol Biol Computac Estruct,) Molecular Informatics 30.6-7: 506-519. Wiley-V CH Verlag GMBH. (Jun. 2011) (Year: 2011).

Mori et al., "What is Mash-up?", A Web 2.0 service construction technique, internet magazine, Impress Corporation, Apr. 1, 2006, No. 135, with English Translation, 54 pages.

\* cited by examiner

Office Visit

1/22/2010

Sample, Joan    DOB: 1/26/1941

Chief Complaint: Discuss Dr. W office visit 1-21-10

HPI:

Pt saw Dr. W – He recommended Lidocaine patch for shin pain/peripheral neuropathy. To see Feb 2nd for a trial for medication Actiq 200 mcg and Ultracet 37.5/325 mg. She is not comfortable with Actiq trial.

PMH:

1 – Dry macular degeneration
2 – Aortic stenosis – Dr. W last echo 11/09 mild to mod AS with nl LV function
3 – DM_ diet control
4 – Atypical chest pain, abnl stress test with Dr. W but declines cath
5 – Osteopenia – intolerant of bisphosphonates – Dr. T

Meds:

Vytorin 10/20
Cozaar 50 mg
Norvasc 5 mg
Lidocaine patch per Dr. W
Ultracet 37.5/325 mg has not tried yet

BP 152/88, P76, R 16

Impression: Follow up visit

1 – Hypothyroidsim – Stable on alternating dose of 75 mcg and 100 mcg
2 – Back and hip pain: Scheduled with Dr. L for March. Trial of Ultracet and Percocet, Lidocaine patch
3 – DM – Diet controlled diabetes. Saw Dr. T. Sees optho regularily (also has history of dry macular degeneration)

Digitaly signed by:

dt  1/22/2010

---

Event: Diabetes Mellitus
ExtractionUUID:
   29629-260270-295926
Model: disMgmt_20140101
_V1.3.21

Annotation: Yes
AnnotatorUUID:
   97e52-592862-97ac22
Annotation_Date: 03/21/2014
Confidence_Level: 99%

DocumentUUID:
   200227-95622017-28992

Office Visit

1/22/2010

Sample, Joan          DOB: 1/26/1941

Chief Complaint: Discuss Dr. W office visit 1-21-10

HPI:

Pt saw Dr. W -- He recommended Lidocaine patch for shin pain/peripheral neuropathy. To see Feb 2nd for a trial for medication Actiq 200 mcg and Ultracet 37.5/325 mg. She is not comfortable with Actiq trial.

PMH:

1 -- Dry macular degeneration
2 -- Aortic stenosis -- Dr. W last echo 11/09 mild to mod AS with nl LV function
3 -- DM_ diet control
4 -- Atypical chest pain, abnl stress test with Dr. W but declines cath
5 -- Osteopenia -- intolerant of bisphosphonates -- Dr. T

Meds:

Vytorin 10/20
Cozaar 50 mg
Norvasc 5 mg
Lidocaine patch per Dr. W
Ultracet 37.5/325 mg has not tried yet

BP 152/88, P76, R 16

Impression: Follow up visit

1 -- Hypothyroidsim -- Stable on alternating dose of 75 mcg and 100 mcg
2 -- Back and hip pain: Scheduled with Dr. L for March. Trial of Ultracet and Percocet, Lidocaine patch
3 -- DM -- Diet controlled diabetes. Saw Dr. T. Sees optho regulariliy (also has history of dry macular degeneration)

Digitaly signed by:

dt  1/22/2010

DM_diet control
- condition only
- documentation
- both

Does this document contain: Diabetes Mellitus ?

Context:
- ☐ Disease Mgmt
- ☒ HCC
- ☐ HEDIS

Comments:

DocumentUUID:
200227-95622017-28992
...

Select all relevant documentation

Fig. 15

Office Visit

1/22/2010

Sample, Joan     DOB: 1/26/1941

Chief Complaint: Discuss Dr. W office visit 1-21-10

HPI:

Pt saw Dr. W – He recommended Lidocaine patch for shin pain/peripheral neuropathy. To see Feb 2nd for a trial for medication Actiq 200 mcg and Ultracet 37.5/325 mg. She is not comfortable with Actiq trial.

PMH:

1 – Dry macular degeneration
2 – Aortic stenosis – Dr. W last echo 11/09 mild to mod AS with nl LV function
3 – DM – diet control
4 – Atypical chest pain, abnl stress test with Dr. W but declines cath
5 – Osteopenia – intolerant of bisphosphonates – Dr. T

Meds:

Vytorin 10/20
Cozaar 50 mg
Norvasc 5 mg
Lidocaine patch per Dr. W
Ultracet 37.5/325 mg has not tried yet

BP 152/88, P76, R 16

Impression: Follow up visit

1 – Hypothyroidsim – Stable on alternating dose of 75 mcg and 100 mcg
2 – Back and hip pain: Scheduled with Dr. L for March. Trial of Ultracet and Percocet, Lidocaine patch
3 – DM – Diet controlled diabetes. Saw Dr. T. Sees optho regularily (also has history of dry macular degeneration)

Digitaly signed by:

dt 1/22/2010

---

Does this document contain:
Diabetes Mellitus ?

Accept

Reject

Context: ☒ Disease Mgmt
    ☐ HCC
    ☐ HEDIS

Comments:

DocumentUUID:
200227-95622017-28992

Fig. 16

Office Visit

1/22/2010

Sample, Joan    DOB: 1/26/1941

Chief Complaint: Discuss Dr. W office visit 1-21-10

HPI:

Pt saw Dr. W – He recommended Lidocaine patch for shin pain/peripheral neuropathy. To see Feb 2nd for a trial for medication Actiq 200 mcg and Ultracet 37.5/325 mg. She is not comfortable with Actiq trial.

PMH:

1 – Dry macular degeneration
2 – Aortic stenosis – Dr. W last echo 11/09 mild to mod AS with nl LV function
3 – DM_ diet control
4 – Atypical chest pain, abnl stress test with Dr. W but declines cath
5 – Osteopenia – intolerant of bisphosphonates – Dr. T

Meds:

Vytorin 10/20
Cozaar 50 mg
Norvasc 5 mg
Lidocaine patch per Dr. W
Ultracet 37.5/325 mg has not tried yet

BP 152/88, P76, R 16

Impression: Follow up visit

1 – Hypothyroidsim – Stable on alternating dose of 75 mcg and 100 mcg
2 – Back and hip pain: Scheduled with Dr. L for March. Trial of Ultracet and Percocet, Lidocaine patch
3 – DM – Diet controlled diabetes. Saw Dr. T. Sees optho regularily (also has history of dry macular degeneration)

Digitaly signed by:

dt 1/22/2010

---

Event: Diabetes Mellitus
ExtractionUUID:
29629-260270-295926
Model: disMgmt_20140101
V1.3.21

Annotation: No

[Refer for Annotation]

DocumentUUID:
200227-95622017-28992
...

Fig. 17

| 1 | 2 | 3 | 4 | 5 | 6 | 7 | 8 | 9 | 10 | 11 | 12 |
|---|---|---|---|---|---|---|---|---|---|---|---|
| Name | DOC SM | BP DATE | BP/s | BP/d | LDL Date | LDL | A1c DATE | A1c | DIABETIC | SMOKER | DATE ASKED IF SMOKES |
| Patient A | NO | 2/1/2011 | 127 | 70 | 11/30/2010 | 93 | | | NO | NO | 11/30/2010 |
| Patient B | YES | 2/15/2011 | 110 | 55 | 2/15/2011 | 145 | 9/25/2010 | 11.3 | YES | YES | 2/15/2011 |
| Patient C | NO | 4/7/2010 | 158 | 87 | 4/11/2010 | 81 | 4/11/2010 | 6.7 | YES | NO | 3/15/2008 |
| Patient D | YES | 1/20/2011 | 148 | 95 | 12/14/2010 | 170 | 12/14/2010 | 8.9 | YES | YES | 12/12/2009 |
| Patient E | NO | 10/28/2010 | 129 | 72 | 12/10/2010 | 54 | 12/10/2010 | 9.6 | YES | YES | 3/30/2010 |
| Patient F | NO | 8/21/2010 | 125 | 88 | 4/20/2009 | 125 | | | NO | NO | |
| Patient G | YES | 6/24/2010 | 149 | 85 | 4/16/2009 | 102 | | | NO | NO | 10/5/2008 |
| Patient H | NO | 3/5/2011 | 147 | 90 | 3/5/2011 | 81 | 3/5/2011 | 12.1 | YES | NO | 3/5/2011 |
| Patient I | NO | 1/28/2010 | 120 | 64 | 2/2/2010 | 65 | | | NO | NO | 12/22/2004 |
| Patient J | YES | 1/5/2011 | 117 | 81 | 1/5/2011 | 112 | 1/5/2011 | 5.9 | YES | YES | |
| Patient K | YES | 7/24/2008 | 152 | 85 | 7/14/2008 | 157 | | | NO | YES | 7/5/2010 |

Fig. 18

SYSTEMS AND METHODS FOR CUSTOMIZED ANNOTATION OF MEDICAL INFORMATION

CROSS-REFERENCE TO RELATED APPLICATIONS

This Continuation Application claims priority of U.S. application Ser. No. 16/784,099, filed on Feb. 6, 2020, of the same title, now U.S. Pat. No. 11,403,330, which claims the benefit of and is a continuation of U.S. application Ser. No. 14/538,798, filed on Nov. 11, 2014, entitled "SYSTEMS AND METHODS FOR CUSTOMIZED ANNOTATION OF MEDICAL INFORMATION", now U.S. Pat. No. 10,580,520, which application is a Non-Provisional Application and claims priority of U.S. Provisional Application No. 62/059,139, filed on Oct. 2, 2014, entitled "SYSTEMS AND METHODS FOR MEDICAL INFORMATION MANAGEMENT".

Also, U.S. application Ser. No. 14/538,798 is a Continuation-in-Part of U.S. application Ser. No. 13/656,652, filed on Oct. 19, 2012, now U.S. Pat. No. 8,898,798, which in turn is a continuation-in-part of U.S. application Ser. No. 13/223,228, filed on Aug. 31, 2011, now U.S. Pat. No. 10,176,541, which claims the benefit of U.S. Provisional Application No. 61/379,228, filed on Sep. 1, 2010. This application Ser. No. 13/656,652 also claims benefit of U.S. Provisional Application No. 61/682,217, filed on Aug. 11, 2012.

Additionally, U.S. application Ser. No. 14/538,798 is a Continuation-in-Part of U.S. application Ser. No. 14/498,594 filed on Sep. 26, 2014, now U.S. Pat. No. 10,600,504, which in turn claims the benefit of U.S. Provisional Application No. 61/883,967, filed on Sep. 27, 2013.

All above-referenced applications/patents listed above are hereby fully incorporated in their entirety by this reference.

BACKGROUND

The present invention relates generally to systems and methods for customized annotation of medical records to verify and document clinical conditions. The present systems and methods enable more accurate and rapid capture of MediCare eligible conditions, thereby ensuring providers are more fairly compensated, and ensure that medical records more accurately reflect a patient's condition. The present invention also relates generally to systems and methods for medical information data warehouse management. The present systems and methods enable more accurate and efficient review of medical evidence contained in the warehouse. Since these documents are often in a variety of formats, and typically include images, scans and freeform text, access of important information from these records is often difficult. Lastly, the present invention relates generally to systems and methods for a medical coder marketplace. The present systems and methods enable more accurate and rapid coding of medical records, capitalizing on a broader pool of coders than is typically available to a provider.

Despite rapid growth of innovation in other fields in recent decades, the world of medical information, including patient medical records, billing, referrals, and a host of other information, has enjoyed little to no useful consolidation, reliability, or ease-of-access, leaving medical professionals, hospitals, clinics, and even insurance companies with many issues, such as unreliability of medical information, uncertainty of diagnosis, lack of standard, and a slew of other related problems.

One common problem with the analysis of medical records is that identification of clinically pertinent conditions is often not properly identified, and further, even when identified, the evidence in the patient records to support such a finding is not always properly referenced. Moreover, the process for verifying a condition is often time consuming and labor intensive. This results in a few issues, including: MediCare compensation difficulties, missing of important health conditions and/or misdiagnosis, and lastly the clouding of medical analytics with incomplete or incorrect data.

The first issue, compensation by MediCare, results in providers being underpaid for work performed. This may cause many providers to shy away from MediCare patients, increases cost on other patients, and generally leads to inefficiencies in the administration of government backed medical coverage.

The second issue, improper or incomplete diagnosis, can be extremely detrimental to the patient. Often early treatment of a condition results in a far better prognosis for the patient. In the extreme, delays of treatment may reduce the patient's life expectancy. As such, there is a very compelling reason to ensure the medical information of a patient is properly documented, with a high degree of accuracy.

In addition to these direct health impacts to the patient, improper or incomplete diagnosis of the patient can lead to unnecessary tests or follow-ups, which can be financially taxing as well as a drain on the resources of the medical community. Thus there are also tangible financial implications to proper diagnosis with supporting evidence.

Lastly, incorrect or missing data may result in the skewing of analytics performed using the medical records. The medical community is entering into an age of big data analysis. These analyses of large data sets of aggregated medical records generated best practices and means for refining a medical practice. It also enables early detection of health trends and patient behavior. Using these results, medical professionals have the opportunity to greatly increase the efficiency of the administration of medical services. This translates directly into improved patient care at reduced costs. However, such analysis relies upon datasets that are accurate. When the input data is flawed, or incomplete, the analysis suffers.

It is therefore apparent that an urgent need exists for improving medical records identification and validation based on evidentiary support of conditions. Such improvements may be achieved via a streamlined medical record review, which enables the annotation of findings, and proper documentation of conditions. Such a review process is superior compared to current manual reviews by allowing much faster and more accurate validation of the medical conditions, along with the generation of searchable annotation records.

SUMMARY

To achieve the foregoing and in accordance with the present invention, systems and methods for generating customized annotations of a medical record. Such systems and methods enable more accurate and faster reviews of medical records.

In some embodiments, the system receives a medical record and processes it using a predictive model to identify evidence of a finding. The system then determines whether to have a recall enhancement or validation of a specific finding. Recall enhancement is used to tune or develop the predictive model, while validation is used to rapidly validate the evidence.

The source document is provided to the user and feedback is requested. When asking for validation, the system also highlights the evidence already identified and requests the user to indicate if the evidence is valid for a particular finding. The user may also annotate the evidence using free form text. The evidence highlighted is determined by a confidence threshold, which is dynamic depending upon context of the presentation of the source document. For example, a doctor looking to make a diagnosis may require a different confidence threshold than a health manager seeking to perform outreach to patients that are susceptible to a condition.

If recall enhancement is utilized, the source document is provided and the user is asked to find evidence in the document for a particular finding. The user may then highlight the evidence that supports the finding, and may likewise provide annotations.

Any inputted annotations are associated with the evidence. This association may be employed by downstream analytics and queries in order to enhance the context surrounding the evidence of a finding. All annotations and other feedback may be stored in a data warehouse for later recall.

In other embodiments, the system receives a set of medical record documents. These documents include evidence for one or more findings. Typically medical documents are not in a structured format, and often may include images, hand-written notes, and free form text. The presently disclosed system can take these documents with evidence and perform natural language processing to identify the findings that the evidence supports.

The data set may then be probabilistically transformed into a structured data set (often as a table). This structured data set includes embedded links that reference the source document where the evidence is located. If the finding is supported by multiple articles of evidence, the link will direct the user to the source document with the highest confidence ranking.

If a user selects the link to the evidence, the user may likewise update the finding if needed. Evidence in the source document is highlighted, in some embodiments, for more rapid and efficient user review. The evidence may have associated annotations that are likewise viewable by the user. These annotations may likewise be updated as desired.

In additional embodiments, the system has procedures for certification of a number of medical coders. The basic level certification ensures that all coders have a minimum skill level before being able to partake in the marketplace. The proficiency of the coders is subsequently measured, continually or intermittently. When the system receives medical records in need of coding, the documents can be routed to one or more coders based upon proficiency of the coders, payment model, availability, or some other criteria. Lastly, the system can facilitate a financial transaction between the coder and the provider who supplied the medical records for coding.

Measuring the proficiency of a coder can be done on as broad or as granular a level as desired. For example, coders may be ranked according to medical field expertise, or more broadly on global metrics. Proficiency includes the speed of a coder, as well as accuracy.

Proficiency for a coder is measured by providing the coder a medical record for which the coding is already established. The coder undergoes the coding process and this data is collected by the system. The speed of the coding and the adherence to the established finding may be used to define the coder's metrics.

By knowing coder proficiency the marketplace can ensure that routing of the records is performed in an advantageous manner. For example, in some cases the marketplace may route records with an aim to maximize throughput and/or accuracy. This can be done by comparing the proficiency of coders currently available and routing each record to the most proficient coders as they become available.

In alternate embodiments, record routing may be based upon a market driven model. In these cases the provider may specify who the record goes to (or a class of coders by proficiency rating). A more proficient coder may cost more than less proficient coders, thereby allowing the market to determine the routing of records. In some cases, this may take the form of an auction for the coder's time, either presently or as a futures market.

In some embodiments, it is also possible that providers have records where there is an urgent need to have them coded rapidly. In such instances, for a premium, the records may be distributed across multiple coders simultaneously in order to get back the codes rapidly.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which:

FIGS. 14-18 provide example screenshots of embodiments of the currently disclosed inventions.

DETAILED DESCRIPTION

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "will," "will not," "shall," "shall not," "must," "must not," "first," "initially," "next," "subsequently," "before," "after," "lastly," and "finally," are not meant to limit the scope of the present invention as the embodiments disclosed herein are merely exemplary.

Note that, for the purposes of this disclosure, the term "finding", "opportunity" or "work" may be utilized interchangeably in order to signify work which is assigned to coders for annotation with medical codes. This work includes providing medical records to the coder for which they can identify the medical findings and extrapolate codes for them.

Also note that the following disclosure includes a series of subsections to aid the clarity of the following disclosure. Such subsections are not intended to artificially limit the scope of the disclosure. As such, any disclosure in a particular subsection may be equally applicable to another section as is applicable.

I. Medical Systems

Figure 1:
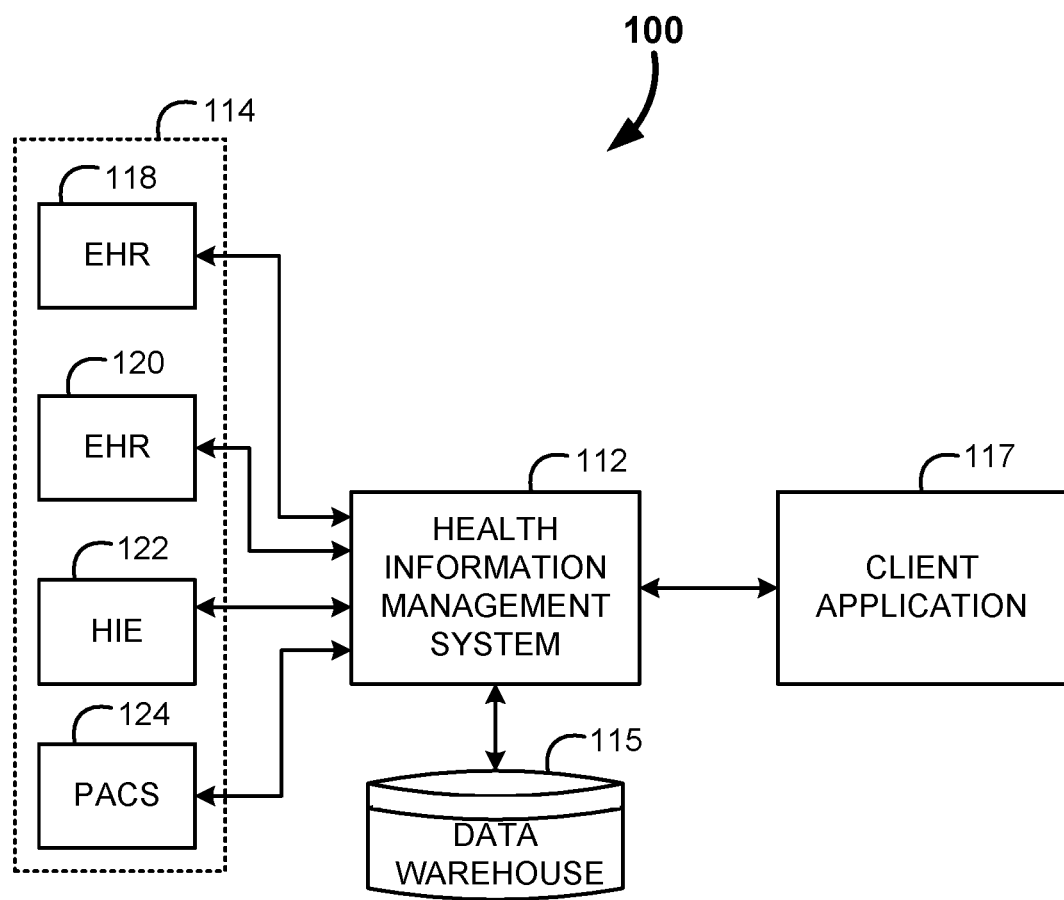
FIG. 1 shows a medical system, in accordance with an embodiment.

Referring now to FIG. 1, a medical system 100 is shown, in accordance with some embodiments. The system 100 is shown to include medical information sources 114, a health information management system 112, and medical information consumers/client applications (also referred to herein as "output" or "medical output") 117. The medical sources 114 are shown to include an electronic health record (EHR) 118, EHR 120, health information exchange (HIE) 122, and a picture archiving and communication system (PACS) 124.

"Medical information", as used herein, may refer to any health-related information, including but not limited to patient medical records, patient entered information, care team entered information, healthcare device generated information, and billing information.

The sources 114 generally provides various medical information to the health information management system 112. For example, the EHRs 118 and 120 each may provide information such as medical records and billing, the HIE 122 may provide information such as medical records, and the PACS 124 may provide information such as diagnostic imaging and reports.

The medical information consumers/client applications 117, which may be made of a host of entities or individuals, such as patients, clinics, medical institutions, health organization, and any other medical-related party, use information that is provided by the health information management system 112. For example, user-customized processed medical information is provided by the health information management system 112 to a number of client applications 117. In this case, the health information management system 112 generates user-customized processed medical information to a plurality of users, with at least a portion of the user-customize processed medical information being provided to each of the users based on the relevancy of the portion being provided of each user's specific function or role and each user's associated security privileges.

In some embodiments, the health information management system may merely be a repository of health records and information. In alternate embodiments, the health information management system 112 may have sophisticated capabilities which enable it to index, map, and consolidate medical information, received from the sources 114, and also potentially enabling the tagging of this information, and reconciliation of the tagged information. In some methods and embodiments, information that is extracted from images is tagged to enhance recall of search queries. Indexing, at least in part, processes document and converts them into formats that allows for quick searching across a large collection of documents.

In some embodiments, the information in the health information management system 112 is encrypted and secure to ensure privacy of sensitive medical information.

It is understood that the sources 114 of FIG. 1 includes merely some examples of the sources that communicate with the health information management system 112 and that other sources, known to those in the field, are contemplated. Similarly, the output 117 may be used by those or entities not discussed herein but that are contemplated and within the scope and spirit of the invention.

Figure 2:
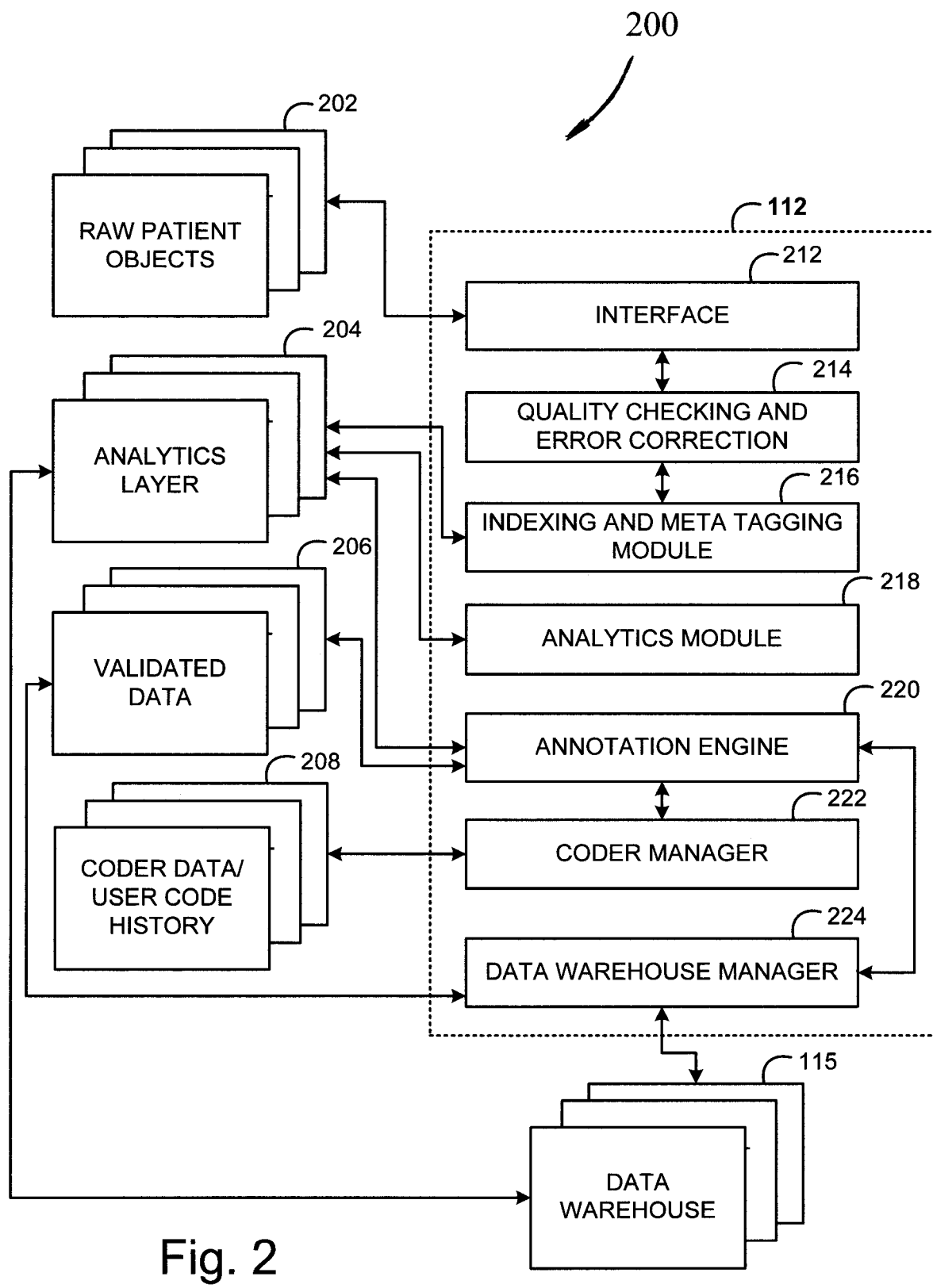
FIG. 2 shows further details of the system within a data architecture, including an annotation engine, coder manager and data warehouse manager, in accordance with an embodiment.

Turning to FIG. 2, a more detailed illustration for the health information management system 112 is provided. In this example diagram, the health information management system 112 is interacting with multiple levels of data storage, shown generally at 200. The storage level begins with raw patient objects 202 which are received from the plurality of sources 114.

The health information management system 112 includes an interface 212 which can collect these objects. These objects 202 may be collected in various forms, such as but not limited to text, html, CCD, CCR, HL7 and any other type or formatted information. The interface 212 then provides to the information to a quality checking and error corrector 214, in some embodiments.

The quality checking and error corrector 214 may simply delete duplicate errors and redundant patient medical records, such as, multiple records for the same individual appearing as though the records are for different individuals, or multiple data elements that are recorded similarly but slightly differently in the different sources. The quality checking and error corrector 214 may also perform other basic and known error correction processes. Alternatively, more advanced quality checking and error corrector 214 systems may check the quality of medical information provided by various sources 114 by the patients, structured data, and unstructured data, in a Wiki-like mannered setting whereby the users can help maintain and improve the quality of information displayed.

In some embodiments, an indexing and Meta tagging module 216 may utilize a processor to processing the data, such as indexing, semantic meta-tagging, and reconciliation. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others. The processed data may then be provided to the second level of the data storage architecture, the analytics layer 204. In some embodiments, the analytics layer 204 may be transient.

An analytics 218 module may take information from the analytics layer 204 and perform certain tasks on the information, which may include query, search, presentation, and quality checking. The output of the analytics 218 may be stored within the analytics layer of the data architecture, or may be stored in a logically separate layer of the data structure, known as the application optimized data.

In some embodiments the analytics module 218 may employ natural language processing (NLP) techniques to parse and syntactically analyze the machine readable records in order to identify medical terms, and apply predictive models to the records to make probabilistic determinations of likely conditions for a patient associated with the medical records. Part of the determination includes assigning a confidence value to the finding based upon historical accuracy of the predictive model and the evidence used to generate the finding. In some embodiments, the analytics module 218 may further be able to parse through multiple medical records, and perform chronological analysis to determine a finding. For example, if a patient is seen for a physical and shows abnormally high glucose levels, and is then scheduled for a follow-up a month later that confirms a diabetic condition, the system may be able to extrapolate that the diabetic condition likely existed as early as the initial physical exam.

It should be noted that many means for NLP are known in the art, and likewise predictive modeling is likewise a rich field. It is intended that any such known art may be employed to effectuate the above disclosed analysis of medical records. This includes adaptive predictive modeling that is updated as additional data becomes available, rule based NLP, etc.

After the medical records have been analyzed for findings, the output may be utilized by an annotation engine 220 to confirm the findings and provide customized annotations to the records. It is currently required that findings used for MediCare compensation be reviewed by a human operator prior to submission. This validation is often time consuming and requires significant coder time and effort to identify the evidence of the finding and properly validate. The annotation engine 220 enables rapid highlighting of the relevant evidence and seamless presentation to the coder for validation and annotation of the evidence. This process has been shown to increase the speed of validation by a coder by twenty to forty times traditional validation processes. In addition, it has been found that the accuracy of findings is increased by these validation processes. Results of the validation and associated annotations may be incorporated into a final data wrapper stored in a data warehouse 115. The financial implications of this capability are enormous, enabling more efficient healthcare administration.

In some embodiments, a coder manager 222 is capable of administering a third party "coder marketplace" to more effectively provide coding expertise. Typically, providers have one or more internal coders capable of manually parsing through medical records to identify findings. Providers typically lack the analytics needed to properly identify coder work quality, or value provided. The coder manager 222 enables a decentralized coder marketplace where coders are screened for proficiencies, speed and accuracy, and are routed validation requests from any number of providers. Screening employs coder data and user code history 208, which is stored for this purpose.

This decentralized system of a coder marketplace enables more rapid coder attention to a finding than a distributed in-house model, and further enables efficient routing of findings to coders most capable of performing the validation. This again, increases validation efficiency, thereby improving the administration of healthcare.

The coder manager 222 may employ many of the systems and methods previously disclosed in co-pending application Ser. No. 14/498,594 entitled "Methods and Systems for Sorting Findings to Medical Coders", which is hereby incorporated by reference.

Regardless of who performs the validation, the validated finding, annotation (if provided), and associated documents are stored within a data warehouse 115. A data warehouse manager 224 may access this data warehouse 115 in order to enable NLP probabilistic transformation of the source documents into a standardized and structured data set. The structured data set includes links from the extracted values to the source documents, thereby enabling a user to rapidly reference back to the source for a given finding. When referencing the source documentation the user may update the information, including the addition of annotations, when required, and ensures that data is provided to the user in the most efficient means possible. In alternate embodiments, the data warehouse manager 224 is able to provide non-validated, annotated records for coder review, and subsequent validation.

Below, each of the annotation engine 220, coder manager 222, and data warehouse manager 224 will be provided in greater detail. These detailed descriptions of these system components are provided by way of example, and it is understood that other logical and/or physical configurations are considered within the scope of this disclosure.

1) Annotation Engine

Figure 3:
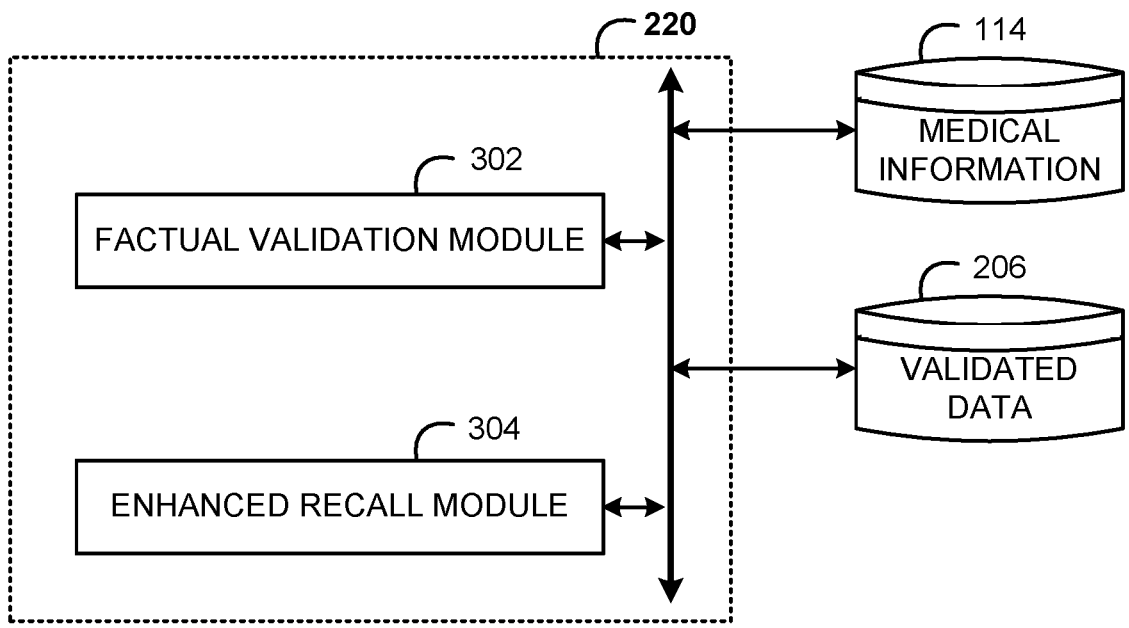
FIG. 3 shows an exemplary embodiment of the annotation engine, in accordance with an embodiment.

FIG. 3 provides a more detailed block diagram of an embodiment of the annotation engine 220. In this example, medical information 114 is provided in either raw form, or as an analyzed form, as previously disclosed. In order to perform annotation, a set of findings is typically required. These findings may be provided from an analytics module which employs predictive modeling to generate findings, as previously disclosed, or the findings may have been identified via more traditional means, such as manual analysis of the medical records by coder.

The annotation engine 220 includes two logically distinct subcomponents, a factual validation module 302 and an enhanced recall module 304. The subsystems may operate in tandem to generate validated and annotated data 206 as a final output. The validated data may include the validated finding, any associated annotations, and associated evidence/documents.

The factual validation module 302 takes a finding and highlights the evidence for the coder. The highlighting may include literally highlighting of the evidence in a source document, or may include other known techniques to readily display pertinent evidence. When more than one source of evidence is available for the specific finding, the system may present the evidence that is most compelling. In the case where a predictive model has been utilized to make the finding, the evidence associated with the highest confidence rating may be displayed. When the finding has been generated by human coders, analytics regarding coder accuracy may be employed to present the "best" coder's evidence.

Alternate evidence may likewise be made available to the user performing the validation as a hyperlink or embedded attachment.

The coder performing the validation may be queried whether the finding is correct via a simple yes/no selection option, or may include a more elaborate toggle option for more granular validation.

The enhanced recall module 304 operates in a reverse order by presenting the coder with a finding and a source document, and requesting the coder to validate by highlighting or otherwise flagging the evidence relevant to the finding. This method of validation may be performed in conjunction with, or as an alternate to the specific finding validation process described previously. Recall enhancing mode is used when a model is being developed or in order to validate a known model to identify when the model needs enhancement. This is an iterative process. Factual validation mode is used to refine an existing model by further classifying accuracy of output. This information can be used in the final presentation of a specific result and in an iterative process to improve the accuracy of the model, taking into account the validation data from multiple coders (annotators).

Annotations supplied during factual validation or enhanced recall may be accepted in a free-form customized format. These annotations, and their associations to a particular piece of evidence in a source document, are stored. The annotations may be queried, and the association may be utilized to inform the importance of a particular piece of evidence.

As previously mentioned, predictive models may be employed to determine what evidence is highlighted for the coder before asking for a diagnosis. Likewise predictive models may be employed to determine which source documentation may be presented when a highlight request is made. One unique feature of this system is that the model used, or weights within the model, may be driven by the context of the annotation activity and/or the user engaging the system.

For example, if an annotation is being performed for a MediCare level submission, the predictive model employed will require a higher threshold of confidence, located in a single medical document. This may result in relatively few medical records being identified for annotation compared to a program for identifying patients for follow-up activity related to potential diabetes risk. In such a context, the evidence may have a lower threshold, and may be collected from multiple documents associated with the patient.

2) Coder Marketplace System

Figure 4:
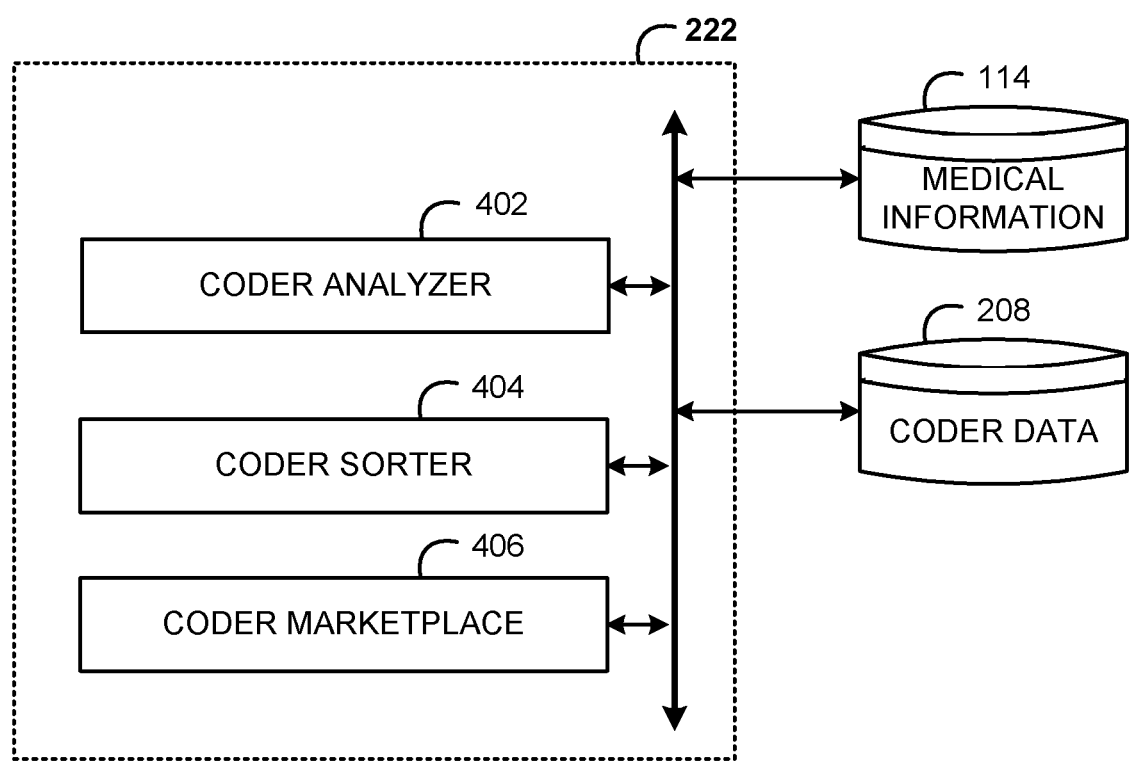
FIG. 4 shows an exemplary embodiment of the coder manager, in accordance with an embodiment.

FIG. 4 provides a more detailed disclosure of the coder manager 222 which is capable of constructing and managing a coder marketplace. The coder manager 222 includes a coder analyzer 402, a coder sorter 404 and a coder marketplace 406 logically coupled. Coder data 208 is utilized to analyze coders based upon their performance coding documents with known codes. Historical coding activity for each coder may also be compared to subsequent review cycles in order to determine coder performance. Metrics for coder proficiency areas, accuracy for the associated areas, time the coder takes to perform, etc. are compiled. This activity of generating coder metrics has been previously disclosed in application Ser. No. 14/498,594 as an 'exploration' of coder ability The coder sorter 404 used the metrics compiled during exploration in order to efficiently delegate findings to an appropriate coder based upon proficiency, speed and accuracy. The coder marketplace 406 is a staging ground where the coders can interface with the system to receive a finding for their review. In order to be eligible to enter the marketplace, coders may be required to complete a certification process, and their rankings may be employed to designate their "class" of coder. For example, the most accurate and rapid coders may be assigned a gold status, whereas less proficient coders are silver, then bronze, for example. Certification and coder ranking provides transparency of coder expertise to providers who rely upon the coder marketplace. Rankings result from both certification and ongoing work done in the marketplace. Specifically, multiple coders can be presented with the same task or evidence and individual accuracy and speed measures can be calculated based upon global statistics on agreement and disagreement among coder. An example of another factor that could influence a coder's ranking is coding supervisor disagreement with annotation. The rate at which each coder's annotations are overridden by a supervisor can impact that coder's ranking.

The routing of findings for coder review may include an optimization of multiple factors. For example, the Risk Adjustment Factor (RAF) for MediCare is a known value. The number of RAF's completed by the coder can be measured (as RAF per hour), as can expected false positive values. By convolving these three factors for a coder, the efficiency of the coder may be computed. If this value is known for all coders available, they can be assigned findings which maximize their return. In this manner coders can review documents much more rapidly, particularly when the findings include highlighted evidence to further streamline review.

3) Coder Rate and Market-Based Pricing

Coder time for projects in the marketplace can be bid upon by consumers (or can be based on supply and demand) and pricing will depend on such factors as availability of each coder's time, the ranking of the coder, the coder's areas of expertise (e.g. HCC, E&M, DRG, disease categories, etc.), familiarity with source data and other factors that might be tracked in the marketplace. Transactional instruments, such as options on coder time and coder time futures, may be supported by the marketplace. In the case of futures contracts, rankings play the role of normalizing contract delivery in much the same way that commodity standards (e.g., prime beef vs. choice beef) are used in the commodities futures markets.

Additionally, the coder marketplace can support other pricing schemas, such as pricing based upon accuracy of output (for example, via routing evidence to multiple coders) is supported in the marketplace. Another pricing mechanism that may be employed is high-urgency annotations ("STAT FACTS"). For these high-urgency situations the marketplace may charge a premium for urgent annotation activities. In such coding environments the system may present a single source of evidence in parallel to multitask the annotation process when time is of the essence.

4) Data Warehouse Manager

Figure 5:
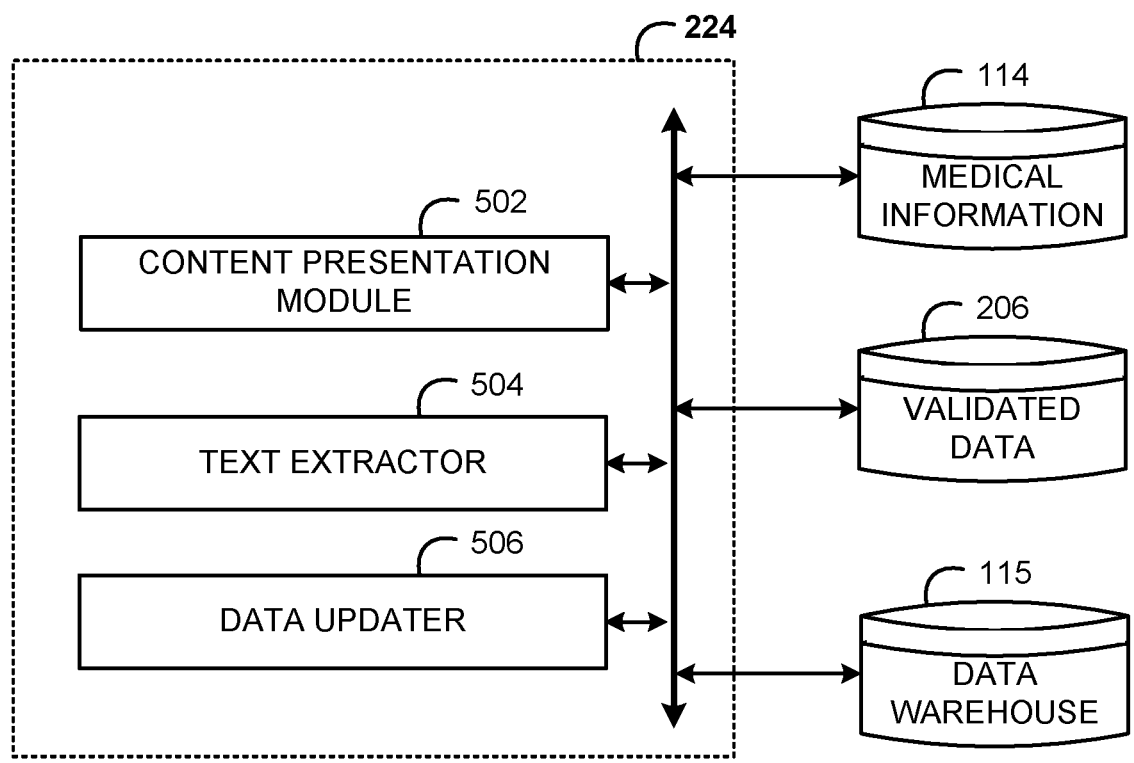
FIG. 5 shows an exemplary embodiment of the data warehouse manager, in accordance with an embodiment.

FIG. 5 provides more detail of the data warehouse manager 224. This system includes a content presentation module 502, a text extractor 504 and a data updater 506 logically coupled together. The content presentation module 502 is enabled to take data from the data warehouse 115 and present it to the user in a tabular (or other condensed form). The content presentation module 502 presents the results of text processing algorithms (for example, machine learning, natural language processing, text search, etc.) which perform a probabilistic transformation of the source documentation into a more readily machine readable format (structured format). An example of a structured format that is commonly employed would be a spreadsheet or a relational database table.

A text extractor 504 enhances values from text extraction with a link that enables the user to reference the source documentation for the extracted values with a single click. For example, when the data warehouse 115 information is placed into a tabular structured format, the findings in the table may include links that, when clicked upon, directly provide the source documentation to the user. The source documentation may be presented with evidence highlighted, and annotations labeled, in order to facilitate very rapid review of the finding. The highlighting, as previously discussed, may be literal highlighting, or otherwise identify the pertinent evidence within the source documentation.

As previously mentioned, text highlighted may be contextually driven based upon user looking at the document, or other contextual considerations. As with annotations, when multiple evidence sources for the finding are available, the most accurate evidence is presented first, with an option to view additional evidence.

The user may opt to update the data within the source documentation, such as highlighting new or different information, or adding an annotation. If the user inputs data, the data updater 506 stores these newly updated records within the data warehouse 115.

II. Methods

Now that the systems for the health management system have been disclosed in detail, attention will be directed toward the processes of medical record annotation and validation. These processes are provided in conjunction with exemplary flowcharts. These flowcharts are merely examples of specific embodiments of some processes employed to perform the annotation, coder marketplace management, and data warehouse presentation.

As such, the following flowcharts, and associated text, are intended to be merely illustrations of embodiments, and not limiting the scope of the present invention to any specific embodiment.

1) Annotation

Figure 6:
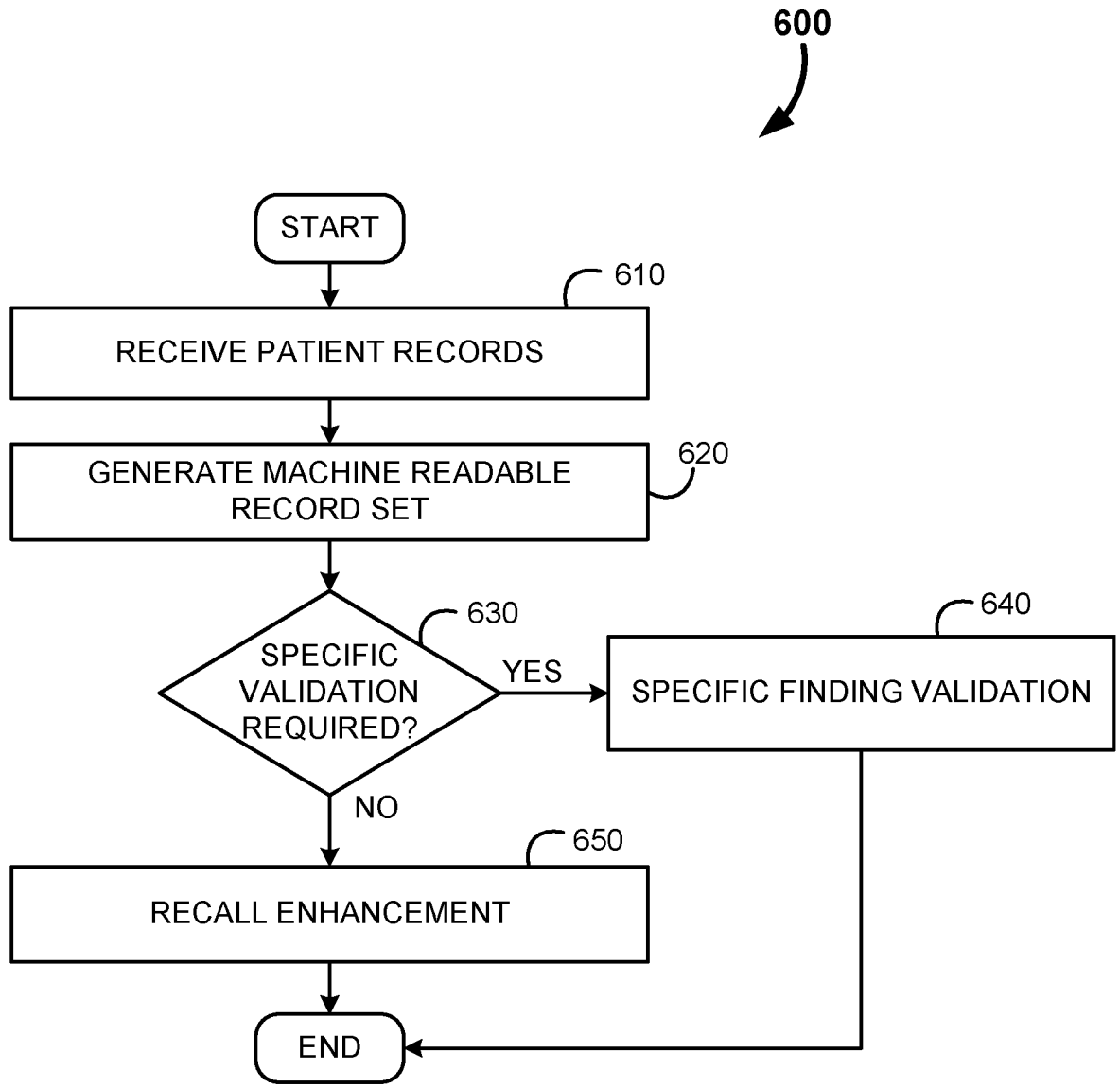
FIGS. 6-9 show example flow charts for the process of annotation and validation of medical codes, in accordance with an embodiment.

FIG. 6 provides a high level overview of one example processes for annotation of findings, provided generally at 600. In this example process, the patient medical records are initially received (at 610) from any of the many sources of medical records previously discussed. The medical records are converted into a machine readable record set (at 620).

The conversion of the data into a machine readable data set may employ known natural language processing techniques, rules based systems, predictive modeling, or any combination thereof. In some embodiments, rule based systems can learn through history, ontology, user-input, the type of user, and a host of other factors, similarities between various information. The system then models the data conceptually by mapping data based on rules for disease/diagnosis relationships, medications, etc. Timing rules may likewise be applied to see how data has changed over time.

Figure 7:
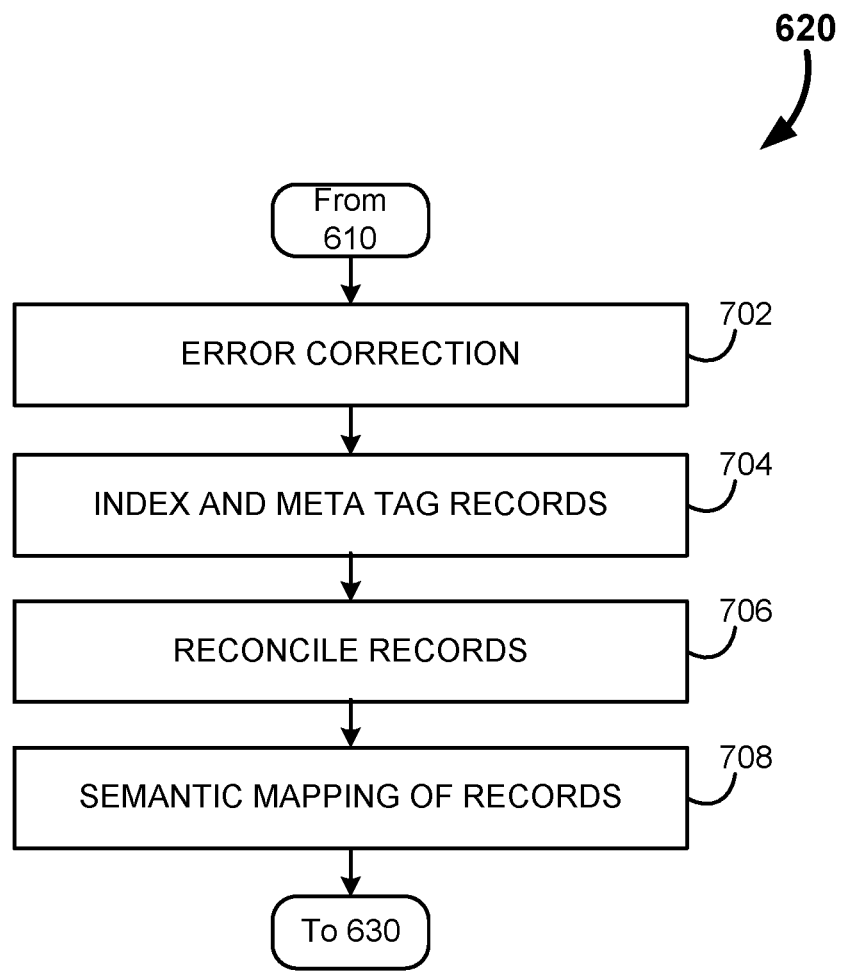

Turning to FIG. 7, a more detailed process flow for the step of converting the medical records into machine readable format is disclosed. Initially an error correction step (at 702) removes duplicate records, incomplete records, and nonsensical records. The corrected records may then be provided for indexing and meta tagging (at 704). Indexing takes processed documents and converts them into formats that make it easy to quickly search across a large collection of documents. Semantic meta-tagging embeds information into the medical information that is relevant thereto and that can be later used to search for certain information for the purpose of reconciliation (at 706) and search, among many others. Next, the records undergo semantic mapping (at 708) as discussed above.

Figure 8:
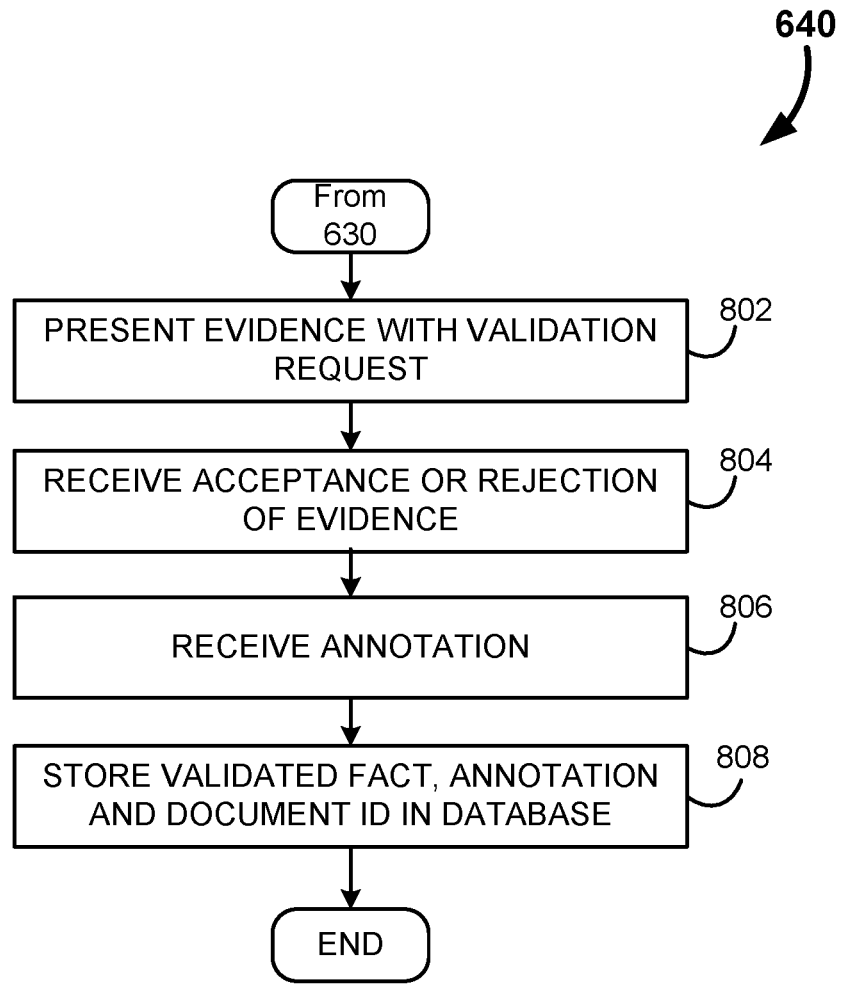
Figure 9:
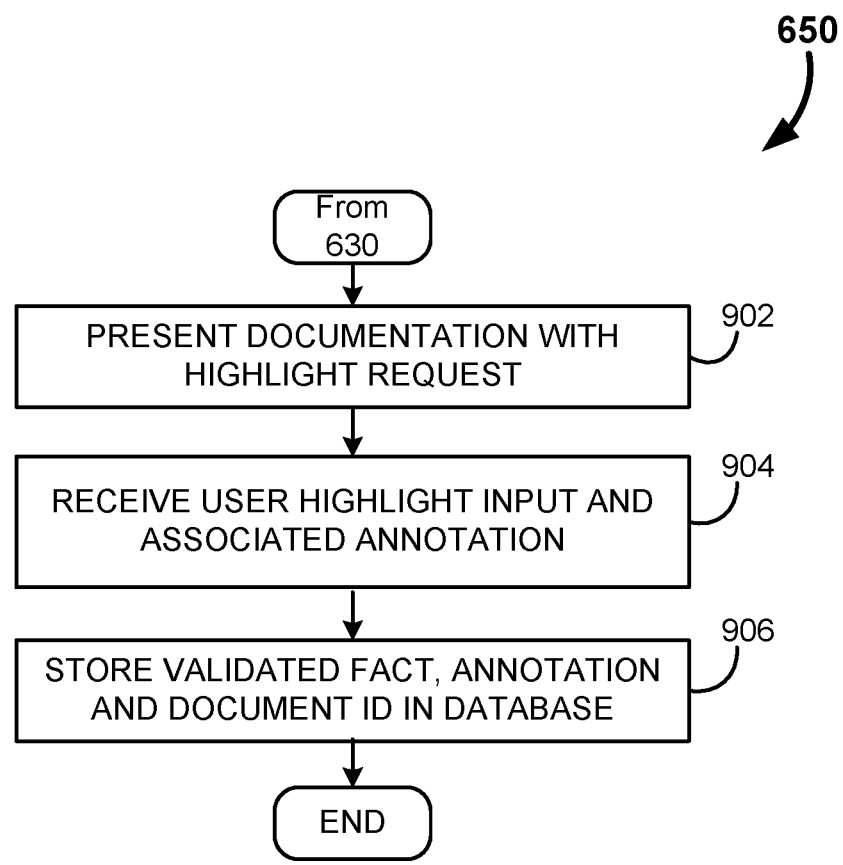

After generating a machine readable data set, it is also possible for the records to be provided to a classifier which identifies findings within the records using predictive models. Returning to FIG. 6, next a query is made whether specific validation of the classification is desired (at 630). If so, the specific finding validation process is performed (at 640). If not, then recall enhancement may be alternately performed (at 650). FIGS. 8 and 9 provide the processes for specific finding validation, and recall enhancement, respectively.

For specific finding validation, at FIG. 8, the evidence is presented to the coder with a validation request (at 802). This evidence typically includes directly providing the source documentation with the specific evidence highlighted, or otherwise identified, so that the coder is immediately directed to the pertinent information. When multiple sources of evidence are present for a finding, the most accurate may be provided to the coder, with a link or other reference to the additional evidence.

The coder is then able to confirm or reject the finding that is provided (at 804). The coder is also able to input any annotations at this stage (at 806). Annotations are customizable free form comments that are associated with a piece of evidence. The annotations are capable of being queried, and the association between the annotation, and highlighted evidence can be leveraged for analytics.

Lastly, the validated fact is stored in the data warehouse, along with any annotations, annotation associations, and document ID (at 808).

In FIG. 9, the process for recall enhancement is provided. In this example process, the source document is provided to the coder with a highlight request (at 902). In many ways this is opposite the specific finding validation procedure detailed above; instead of requesting a validation of a finding based upon provided evidence, here the finding is provided, and the coder is asked to locate the evidence in the source document.

The user then highlights the relevant evidence that supports the finding, and may also input associated annotations with the highlighted evidence (at 904). The validated fact is stored in the data warehouse, along with any annotations, annotation associations, and document ID (at 906).

2) Data Warehouse Presentation and Management

Figure 10:
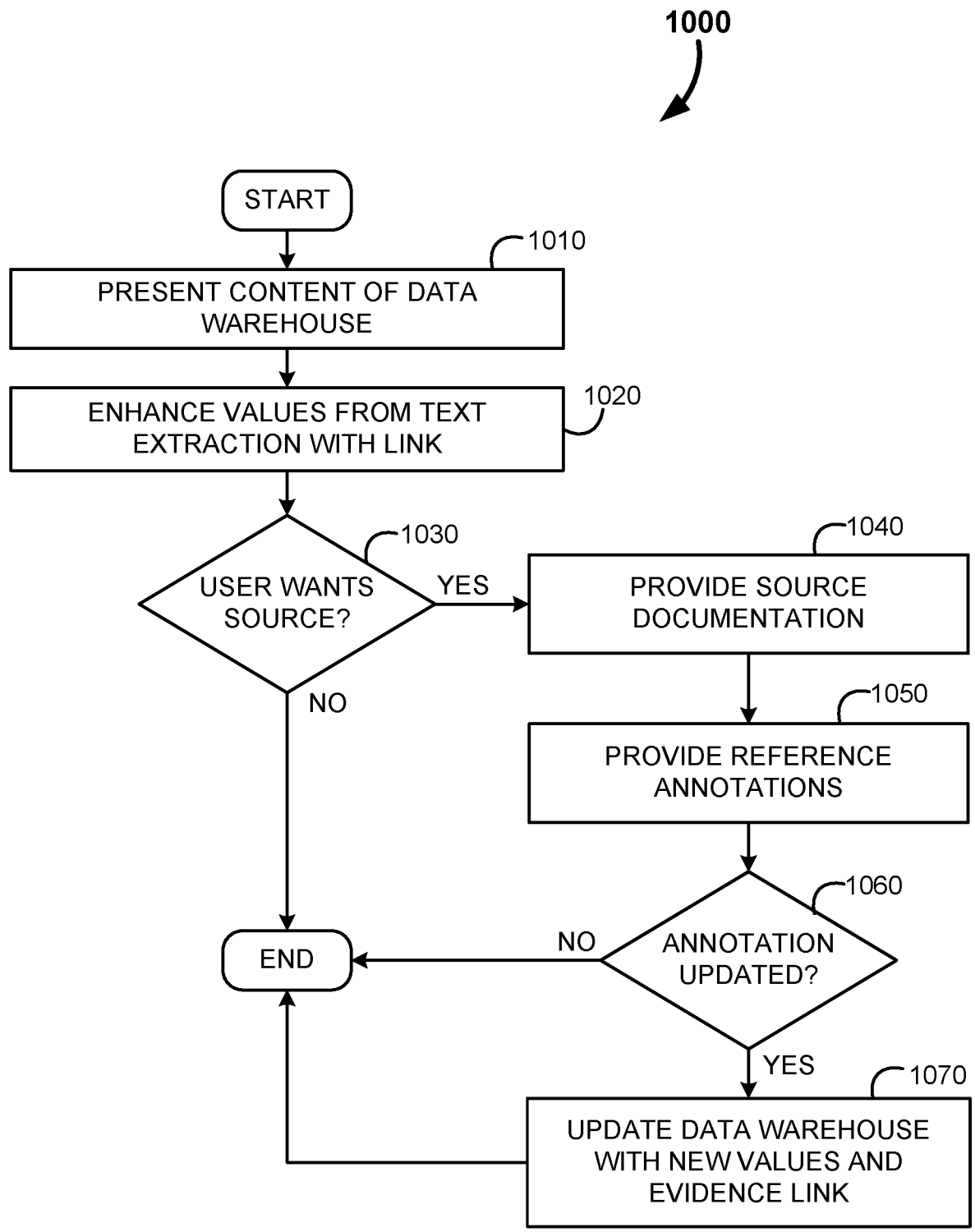
FIG. 10 shows an example flowchart for the process of managing a data warehouse.

FIG. 10 provides the exemplary process of the management of the data warehouse, and particularly how the findings in the source documents may be compiled and presented to the user in a structured format, shown generally at 1000.

This process begins by presenting the content of the data warehouse to the user (at 1010). As previously touched upon, this presentation may include earlier classifications and validations of the source documents in order to generate structured data. In some embodiments, natural language processing and predictive models are leveraged to perform probabilistic transformations of the unstructured source documents (and the evidence they contain) into a structured dataset. In some embodiments, this structured dataset may be a tabular summary of the patients, basic chart information, and whether they suffer from aliments that are designated. In some cases the structured data set is configurable by the user. Additionally, the dataset may further be contextually driven such that the data presented matches the intended end use.

For example, in one instance (disease management use case), the user is a case manager looking to identify diabetic patients for case management. In such a situation the presented data may include a table with basic patient information and a column indicating whether a patient is diabetic or not. Since the case manager benefits from identifying all diabetic patients, the evidentiary threshold used to determine who a diabetic is may be relatively low. In contrast, a cardiologist may be interested in a different pathology, such as acute heart failure, and may desire to have more pinpointed results. As such the columns would reflect this other pathology, and the evidentiary standards may be higher. In turn this could be contrasted with a coder looking for patients with a pathology for MediCare submission, which has yet another evidentiary standard (evidence in a single source document, etc.).

After the structured data set has been generated for presentation, the values within the dataset may be enhanced with a link back to the source documentation (at 1020). Since the structured data set is an abstraction of source documentation, enabling a user to efficiently and rapidly reference the evidence is desirable. This link enables a user to reference the source evidence using a single click of a mouse button if they so desire (at 1030).

If the link is selected, the source document is directly accessed and presented with the evidence highlighted and/or otherwise identified (at 1040). If annotations were included when the source document was originally coded, these annotations can likewise be presented to the user (at 1050). The user than has the option to update the annotations, factual conclusion, etc. (at 1060). For example, a user could identify that the evidence is not properly attributed to the correct pathology, and the annotation and finding can be updated accordingly.

If the annotation and/or finding have been updated by the user, the data warehouse may be updated to reflect these new values and evidence links (at 1070). Thus, the structured data presented to the user will now reflect the correct findings and evidence.

Annotation of data presented by in the data warehouse mode can be used for a number of applications. For example, in the disease management use case described above, classification of patients by the urgency, acuteness and medical priority of their conditions and recent clinical events (current, reliable data vs. stale or inaccurate) may be annotated by a coder or case manager to reflect a difference case management priority or interpretation of the data.

Another application of data annotation in this context is identification of data inconsistencies, stale, incorrect or outdated information (e.g. patient is deceased, or condition no longer applies, as in foot ulcer on a patient with below knee amputation).

Internal audit: Data warehouse management and extracted data annotation can be applied to identification of inefficient, low value or redundant care activities. Value/benefit, ROI classification. (This is an area where chart audits by medical directors could be streamlined into an annotation process.)

3) Coder Marketplace

Figure 11:
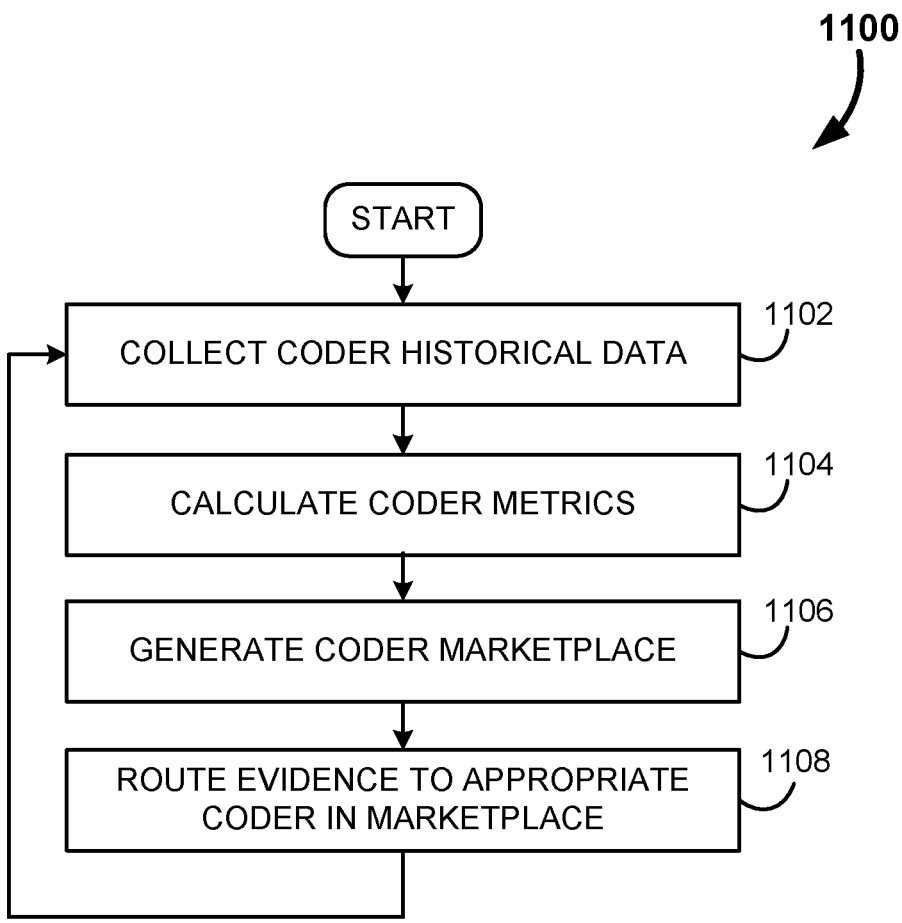
FIGS. 11-13 shows example flowcharts for the process of managing a coder marketplace.

FIG. 11 provides an example process for the generation of a coder marketplace, shown generally at 1100. In this process, the historical coder data is collected (at 1102). This historical data includes coder activity and speed of the coder's activity, at a minimum. Using this coder history, a series of coder metrics may be determined (at 1104).

Figure 12:
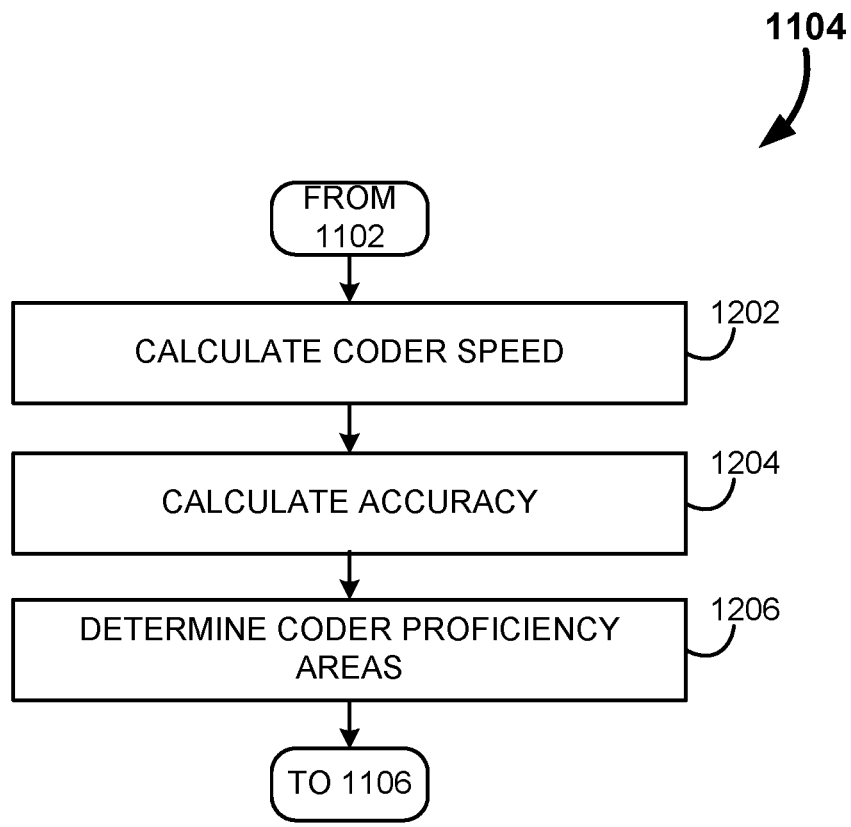

FIG. 12 provides a more detailed example of the process for calculating these coder metrics. For example, the speed that a coder completes the review of a finding may be determined (at 1202). This coder speed value may be an overall speed, or may be broken out into more granular metrics. For example, a coder may be very rapid in making determinations related to oncological fields, but be far slower when dealing with cardiac conditions. Having these more granular metrics based upon medical categories may be particularly beneficial, however there are yet other ways to refine coder metrics, such as speed dependent upon time of the day, day of the week, number of records already coded, etc. It should be understood that the coder's speed metrics may be broken down into as granular a level as is desired for any given objective.

Likewise, coder accuracy may be determined (at 1204) generally, or broken down in the same manner as described for speed metrics. The speed and accuracy metrics may be analyzed to determine areas of coder proficiency (at 1206). Continuing the above example, assume that the coder accuracy is also lower for cardiac findings, and higher for oncology. Also assume that the coder performs 20% better in the afternoon than in the morning. After approximately 3 hours of coding however, the coder's accuracy tends to drop significantly. Using this information, a fairly complete profile of the coder's proficiencies can be generated. In this example, the coder is most efficient when provided cases having to do with oncology, especially in the afternoon for no more than 3 hours at a time. This proficiency profile can be leveraged in order to maximize coder efficiency in a marketplace, as will be described in more detail below.

Returning to FIG. 11, the coder marketplace is generated (at 1106). Ideally, the marketplace is separate from any provider network and includes a large number of coders. By centralizing the marketplace, economy of scale, workload leveling, and other efficiencies can be realized. However, it is entirely within the scope of this \disclosure that a coder marketplace could be set up within a provider network, particularly if the provider network is large.

Coders entered into the network have been screened and certified, in some embodiments. They may also receive additional training. The metrics for the coders, or subsequent performance, may be utilized to rank coders (gold, silver, and bronze, for example). In some embodiments, gamification techniques may be employed within the marketplace to further increase coder efficiency.

Figure 13:
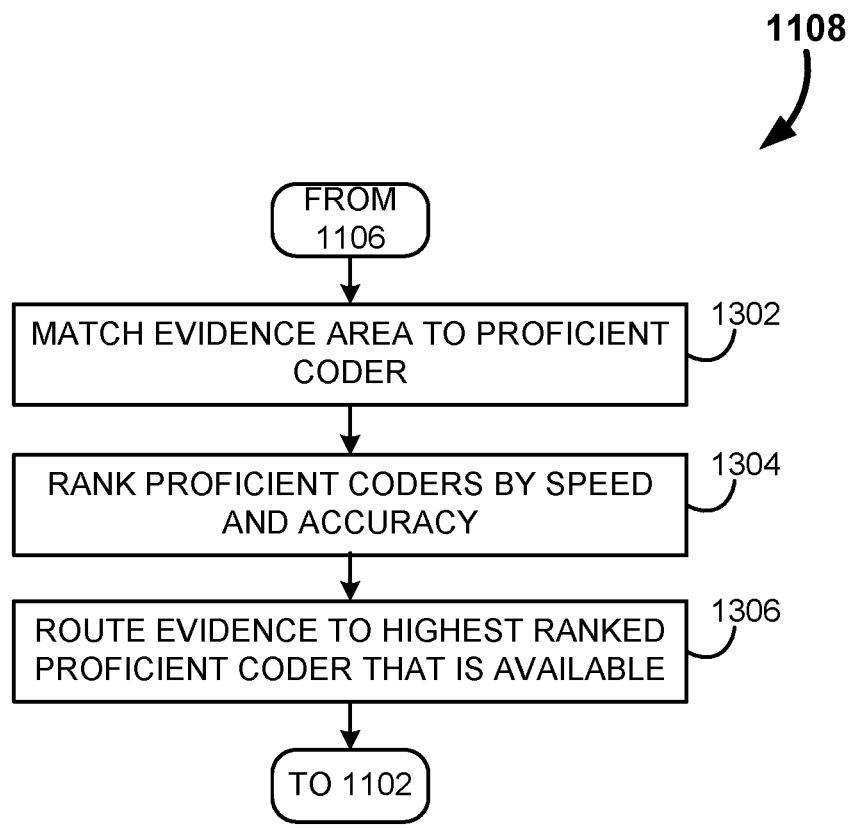

Once the marketplace is available, evidence may be routed to the appropriate coder (at 1108). FIG. 13 provides a more detailed example of this process. Initially, the coders may be narrowed by those who are proficient in the area of the evidence (at 1302). For example, if the evidence is a cardiac condition, our previous hypothetical coder may not be suited to receive the evidence. Next, among the proficient coders identified, they may be ranked by speed and accuracy (at 1304). The evidence is then routed to the highest ranked coder who is available (at 1306). This ensures that the evidence is provided to the best suited coder for handling it. This increases overall accuracy of the coding, as well as optimizes throughput.

A coder marketplace can thus provide the same coder services that are currently being performed by coders, but with enhanced efficiency and accuracy by ensuring that coders are optimally matched with the evidence. By centralizing this process, a large number of coders can be included in the marketplace, thereby ensuring that proficiencies are available for all pathological areas. Additionally, by having a large pool of coders, and a large set of providers supplying evidence, workload leveling can be more efficiently managed.

Moreover, when employing the above described evidentiary validation and data warehouse management techniques, the evidence is presented to the coders already highlighted, thereby increasing coder efficiency significantly.

III. Examples

FIGS. 14-18 provide example screenshots of user views of the system employing annotations and data warehouse management. It should be realized that these screenshots are provided by way of example, and do not restrict the scope of the embodiments.

FIG. 14 provides a screen shot of patient information, shown generally at 1400. The patient record source document is provided at 1402. Evidence has been highlighted at 1404. A finding summary box associated with the evidence is also provided at 1406. The finding summary includes the finding (here diabetes), extraction ID and associated model used in the extraction, If the evidence has been annotated, the ID of the annotator, date of annotation, and confidence level for the finding. The source document ID is also provided.

FIG. 15 provides another screenshot where an embodiment of the specific finding validation is being performed, shown generally at 1500. Like wish the previous screenshot, the source document is provided at 1402, and the evidence is provided as highlighted. Here however, the user is being queried for each piece of highlighted evidence whether the evidence is a condition and/or documentation, shown at the call out boxes 1502. Likewise, the user is being queried whether the document contains a finding for diabetes at 1504. The context of the finding, and a customizable annotation, may also be provided at the query box 1504.

FIG. 16 provides another embodiment for specific finding validation, shown generally at 1600. Again the source document 1402 and the highlighted evidence 1404 are presented to the user. However here, a simple yes/no question is presented to the user at the query box 1602. Context and free-form annotation are also available for the user's input.

FIG. 17 provides a screenshot where no annotation has been provided, and the user may select to refer out the evidence for annotation, shown generally at 1700. Again, the evidence 1404 is shown highlighted in the source document 1402. The summary box 1702 includes the finding, extraction ID and model. However, here it is indicated that no annotation is available, and the user has a button that allows them to refer the evidence out for annotation.

FIG. 18 provides a registry report for the data warehouse, shown generally at 1800. This report is a tabular structured format that has been extracted from the source documents using natural language processing and/or predictive models to perform a probabilistic transformation of the unstructured source data into this registry. In this example, patient name, basic physiological data (blood pressure, dates, cholesterol, A1c, smoking status, etc.) are listed. Additionally, a condition diagnosis is provided in the table as a simple "yes/no" selection. These diagnoses have been generated using the evidence in the source document(s). These diagnoses are linked, allowing the user to reference the source document, with a single click, from this structured data set. When a link is selected, the source document is presented with the evidence highlighted in a manner similar to what is shown in FIG. 14.

IV. System Embodiments

Figure 19A:
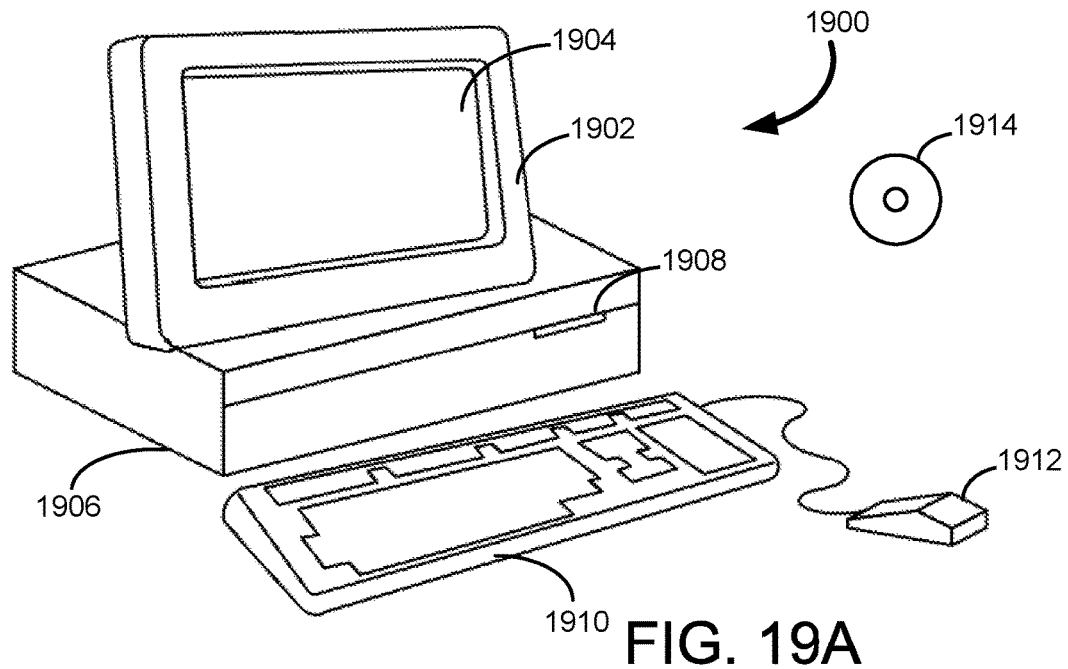
FIGS. 19A and 19B are example illustrations of a computer system capable of embodying the current invention.
Figure 19B:
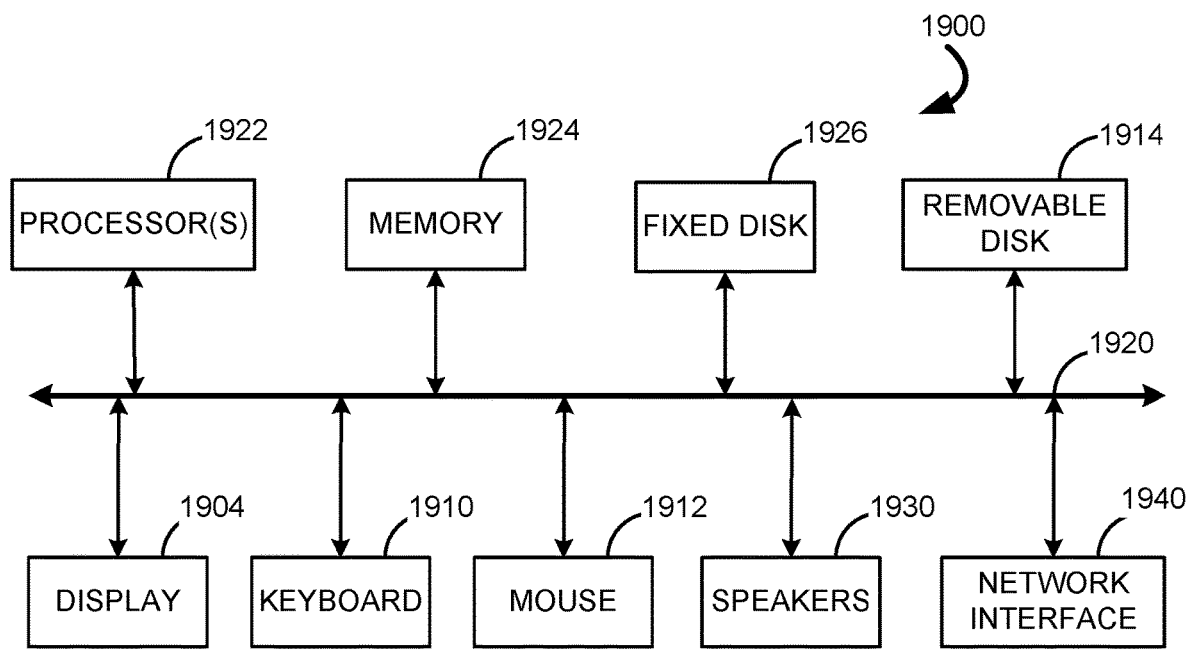

FIGS. 19A and 19B illustrate a Computer System 1900, which is suitable for implementing embodiments of the present invention. FIG. 19A shows one possible physical form of the Computer System 1900. Of course, the Computer System 1900 may have many physical forms ranging from a printed circuit board, an integrated circuit, and a small handheld device up to a huge super computer. Computer system 1900 may include a Monitor 1902, a Display 1904, a Housing 1906, a Disk Drive 1908, a Keyboard 1910, and a Mouse 1912. Disk 1914 is a computer-readable medium used to transfer data to and from Computer System 1900.

FIG. 19B is an example of a block diagram for Computer System 1900. Attached to System Bus 1920 are a wide variety of subsystems. Processor(s) 1922 (also referred to as central processing units, or CPUs) are coupled to storage devices, including Memory 1924. Memory 1924 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A Fixed Disk 1926 may also be coupled bi-directionally to the Processor 1922; it provides additional data storage capacity and may also include any of the computer-readable media described below. Fixed Disk 1926 may be used to store programs, data, and the like and is typically a secondary storage medium (such as a hard disk) that is slower than primary storage. It will be appreciated that the information retained within Fixed Disk 1926 may, in appropriate cases, be incorporated in standard fashion as virtual memory in Memory 1924. Removable Disk 1914 may take the form of any of the computer-readable media described below.

Processor 1922 is also coupled to a variety of input/output devices, such as Display 1904, Keyboard 1910, Mouse 1912 and Speakers 1930. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, motion sensors, brain wave readers, or other computers. Processor 1922 optionally may be coupled to another computer or telecommunications network using Network Interface 1940. With such a Network Interface 1940, it is contemplated that the Processor 1922 might receive information from the network, or might output information to the network in the course of performing the above-described validation and data warehouse management. Furthermore, method embodiments of the present invention may execute solely upon Processor 1922 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A computer-implemented method implemented by a health information system including a processor, the method for generating customized annotations of a medical record, the method comprising:
   converting, by the processor, a medical record source document into a standardized formatted medical record source document by indexing, by the processor, the medical record source document;
   applying, by the processor, a predictive model to the standardized formatted medical record source document;
   identifying, by the processor based on the application, evidence for a medical condition finding for a patient associated with the medical record source document;
   generating, by the processor, a query requesting to operate the health information system in one of two modes;
   in response to identifying the evidence and operating the health information system in the one mode, (i) highlighting, by the processor, the evidence for the medical condition finding or (ii) generating, by the processor, a request requesting a user to annotate the standardized formatted medical record source document to identify further evidence for the medical condition finding; and
   causing, by the processor, the highlighted evidence or the request to be displayed on a user computing device.

2. The computer-implemented method of claim 1 further comprising receiving, by the processor via a health information exchange or a picture archiving communication system, the medical record source document as a machine readable record having one of a plurality of formats.

3. The computer-implemented method of claim 1, wherein the two modes include a specific finding validation mode and an enhanced recall mode.

4. The computer-implemented method of claim 3 further comprising highlighting, by the processor, the evidence for the medical condition finding in response to operating the health information system in the specific finding validation mode.

5. The computer-implemented method of claim 3, wherein operating in the specific finding validation mode further comprises:
   generating an additional request requesting the user to input in the health information system whether the finding is valid based upon the highlighted evidence.

6. The computer-implemented method of claim 3 further comprising generating, by the processor, the request requesting the user to annotate the standardized formatted medical record source document in response to operating the health information system in the enhanced recall mode.

7. The computer-implemented method of claim 3 further comprising generating, by the processor, a further request requesting the user to highlight the standardized formatted medical record source document in response to operating the health information system in the enhanced recall mode.

8. A health information system for generating customized annotations for a record, the health information system comprising a processor configured to:
   convert a medical record source document into a standardized formatted medical record source document by indexing, by the processor, the medical record source document;
   apply a predictive model to the standardized formatted medical record source document;
   identify, based on the application, evidence for a medical condition finding for a patient associated with the medical record source document;
   generate a query requesting to operate the health information system in one of two modes;
   in response to identifying the evidence and operating the health information system in the one mode, (i) highlight the evidence for the medical condition finding or (ii) generate a request requesting a user to annotate the standardized formatted medical record source document to identify further evidence for the medical condition finding; and
   cause the highlighted evidence or the request to be displayed on a user computing device.

9. The health information system of claim 8, wherein the processor is further configured to receive, via a health information exchange or a picture archiving communication system, the medical record source document as a machine readable record having one of a plurality of formats.

10. The health information system of claim 8, wherein the two modes include a specific finding validation mode and an enhanced recall mode.

11. The health information system of claim 10, wherein the processor is further configured to highlight the evidence for the medical condition finding in response to operating the health information system in the specific finding validation mode.

12. The health information system of claim 10, wherein operating in the specific finding validation mode further comprises:
   generating an additional request requesting the user to input in the health information system whether the finding is valid based upon the highlighted evidence.

13. The health information system of claim 10, wherein the processor is further configured to generate the request requesting the user to annotate the standardized formatted medical record source document in response to operating the health information system in the enhanced recall mode.

14. The health information system of claim 10, wherein the processor is further configured to generate a further request requesting the user to highlight the standardized formatted medical record source document in response to operating the health information system in the enhanced recall mode.

15. At least one non-transitory computer-readable storage medium having computer-executable instructions embodied thereon, wherein when executed by a processor of a health information system for generating customized annotations for a record, the computer-executable instructions cause the processor to:
- convert a medical record source document into a standardized formatted medical record source document by indexing, by the processor, the medical record source document;
- apply a predictive model to the standardized formatted medical record source document;
- identify, based on the application, evidence for a medical condition finding for a patient associated with the medical record source document;
- generate a query requesting to operate the health information system in one of two modes; and
- in response to identifying the evidence and operating the health information system in the one mode, (i) highlight the evidence for the medical condition finding or (ii) generate a request requesting a user to annotate the standardized formatted medical record source document to identify further evidence for the medical condition finding; and
- cause the highlighted evidence or the request to be displayed on a user computing device.

16. The computer-readable storage medium of claim 15, wherein the computer-executable instructions further cause the processor to receive, via a health information exchange or a picture archiving communication system, the medical record source document as a machine readable record having one of a plurality of formats.

17. The computer-readable storage medium of claim 15, wherein the two modes include a specific finding validation mode and an enhanced recall mode.

18. The computer-readable storage medium of claim 17, wherein the computer-executable instructions further cause the processor to highlight the evidence for the medical condition finding in response to operating the health information system in the specific finding validation mode.

19. The computer-readable storage medium of claim 17, wherein operating in the specific finding validation mode further comprises:
- generating an additional request requesting the user to input in the health information system whether the finding is valid based upon the highlighted evidence.

20. The computer-readable storage medium of claim 17, wherein the computer-executable instructions further cause the processor to generate the request requesting the user to annotate the standardized formatted medical record source document in response to operating the health information system in the enhanced recall mode.

* * * * *